US00PP22770P2

(12) United States Plant Patent
Smith

(10) Patent No.: US PP22,770 P2
(45) Date of Patent: Jun. 5, 2012

(54) ***CHRYSANTHEMUM* PLANT NAMED 'SYELECT AMBE'**

(50) Latin Name: *Chrysanthemum×morifolium*
Varietal Denomination: Syelect Ambe

(75) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/932,963

(22) Filed: Mar. 10, 2011

(51) Int. Cl.
*A01H 5/00* (2006.01)

(52) U.S. Cl. ..... Plt./287

(58) Field of Classification Search ..... Plt./287
See application file for complete search history.

*Primary Examiner* — Annette Para
(74) *Attorney, Agent, or Firm* — Joshua L. Price

(57) ABSTRACT

A new *Chrysanthemum* plant named 'Syelect Ambe' particularly distinguished by the medium sized yellow and greyed-red colored inflorescences, good mounding plant habit, and an early natural season flowering.

1 Drawing Sheet

Latin name of the genus and species of the plant claimed: *Chrysanthemum×morifolium.*

Varietal denomination: 'Syelect Ambe'.

BACKGROUND OF THE NEW PLANT

The present invention comprises a new *Chrysanthemum*, botanically known as *Chrysanthemum×morifolium*, and hereinafter referred to by the variety name 'Syelect Ambe'.

'Syelect Ambe' is a product of a planned breeding program. The new cultivar has medium sized yellow and greyed-red colored inflorescences, good mounding plant habit, and an early natural season flowering.

'Syelect Ambe' originated from a hybridization made in February 2007 in a controlled breeding environment in Tenjo, Columbia. The female parent was the proprietary plant designated '04-M266', unpatented, with yellow colored inflorescences, smaller plant size and a later natural flowering season.

The male parent of 'Syelect Ambe' was 'Yoursula', U.S. Plant Pat. No. 13,641, with lavender colored inflorescences, more disc florets present, smaller plant size and a about a 10 day later natural flowering season. The resultant seed was sown in June 2007 in Alva, Fla.

'Syelect Ambe' was selected as one flowering plant within the progeny of the stated cross in October 2007 in a controlled environment in Alva, Fla.

The first act of asexual reproduction of 'Syelect Ambe' was accomplished when vegetative cuttings were propagated from the initial selection in November 2007 in a controlled environment in Alva, Fla.

BRIEF SUMMARY OF INVENTION

Horticultural examination of plants grown from cuttings of the plant initiated in November 2007, and continuing thereafter, has demonstrated that the combination of characteristics as herein disclosed for 'Syelect Ambe' are firmly fixed and are retained through successive generations of asexual reproduction.

'Syelect Ambe' has not been observed under all possible environmental conditions. The phenotype may vary significantly with variations in environment such as temperature, light intensity and day length.

A Plant Breeder's Right for this cultivar was applied for in Canada on Mar. 19, 2010 (No. 10-6932). 'Syelect Ambe' has not been made publicly available more than one year prior to the filing of this application.

The following traits have been repeatedly observed and are determined to be basic characteristics of the new variety. The combination of these characteristics distinguishes this *Chrysanthemum* as a new and distinct variety

BRIEF DESCRIPTION OF THE PHOTOGRAPHS

The accompanying photographic drawing shows typical flower and foliage characteristics of 'Syelect Ambe' with colors being as true as possible with an illustration of this type.

The photographic drawing shows a flowering potted plant of the new variety, and a close-up of the flowers.

DETAILED BOTANICAL DESCRIPTION

The plant descriptions, measurements and aforementioned photographs were taken in Gilroy, Calif. in August 2010 under natural light. These plants used in the photograph and descriptions were about 12 weeks old.

Color references are made to The Royal Horticultural Society Colour Chart (R.H.S.) 2001.

TABLE 1

DIFFERENCES BETWEEN THE NEW VARIETY 'SYELECT AMBE' AND A SIMILAR VARIETY

| | 'Syelect Ambe' | 'Ginger' (U.S. Plant Pat. No. 6,403) |
|---|---|---|
| Plant habit: | More compact/more rounded<br>More flowers over whole plant | Less compact/more upright<br>Lacks flowers on the sides of plant |

TABLE 1-continued

DIFFERENCES BETWEEN THE NEW VARIETY 'SYELECT AMBE' AND A SIMILAR VARIETY

| | 'Syelect Ambe' | 'Ginger' (U.S. Plant Pat. No. 6,403) |
|---|---|---|
| Flowering response: | 3 weeks earlier in the south | 3 weeks later in the south |
| Flowering uniformity: | More flowers opening at the same time | Fewer flowers opening at the same time |

Plant:

*Form, growth and habit.*—Herbaceous decorative garden-type; stems upright, rounded and freely branching habit, strong and moderately vigorous growth habit.

*Plant height.*—12-14 cm.

*Plant height (inflorescence included).*—31-35 cm.

*Plant width.*—40-42 cm.

*Garden performance and tolerance to weather.*—Very good.

Roots:

*Number of days to initiate roots.*—4 days at about 22 degrees C.

*Number of days to produce a rooted cutting.*—10-12 days at 22 degrees C.

*Type.*—Fine, fibrous, free branching.

*Color.*—RHS N155B but whiter.

Foliage:

*Arrangement.*—Alternate.

*Immature, leaf color, upper surface.*—Closest to RHS 137A but darker.

*Lower surface.*—Closest to RHS 137B.

*Mature, leaf color, upper surface.*—Closest to RHS 137A but darker.

*Lower surface.*—Closest to RHS 137B.

*Length.*—4.8-5.0 cm.

*Width.*—3.7-3.9 cm.

*Shape.*—Ovate.

*Base shape.*—Attentuate.

*Apex shape.*—Mucronulate.

*Margin.*—Irregularly lobed, slightly palmate.

*Texture, upper surface.*—Heavily bifid T-shaped hairs.

*Lower surface.*—Heavily bifid T-shaped hairs.

*Color of veins, upper surface.*—RHS 147C.

*Color of veins, lower surface.*—RHS 147C; with RHS 137A margins.

*Petiole color.*—RHS 147C.

*Length.*—1.8-2.0 cm.

*Diameter.*—0.3 cm.

*Texture.*—Bifid T-shaped hairs.

Stem:

*Quantity of main branches per plant.*—5 with many secondary branches.

*Color of stem.*—RHS 146A but appears lighter because of hairs.

*Length of stem.*—16-20 cm.

*Diameter.*—0.6-0.7 cm.

*Length of internodes.*—1.3-2.0 cm.

*Texture.*—Bifid T-shaped hairs.

*Color of peduncle.*—RHS 146A but appears lighter because of hairs.

*Length of peduncle.*—12-16 cm.

*Peduncle diameter.*—0.25-0.3 cm.

*Texture.*—Bifid T-shaped hairs.

Inflorescence:

*Type.*—Compositae type, solitary decorative-type inflorescences, borne terminally above foliage, ray florets arranged acropetally on a capitulum.

*Quantity of short days to flowering (response time).*—46 days.

*Natural season flowering.*—Early September.

*Quantity of inflorescences per plant.*—Approximately 120+75 buds.

*Lastingness of individual blooms on the plant.*—About 6 weeks from the first flower.

*Fragrance.*—Slightly spicy.

Bud (just when opening/showing color):

*Color.*—Closest to RHS 181A with hint of RHS 3C basally.

*Length.*—0.8-1.0 cm.

*Width.*—1.0-1.1 cm.

*Shape.*—Oblate.

Immature inflorescence:

*Diameter.*—3.5-4.0 cm.

*Color of ray florets, upper surface.*—RHS 6C with RHS 180A to 180B apex.

*Lower surface.*—RHS 6C with RHS 180A to 180B apex.

Mature inflorescence:

*Diameter.*—5.0-5.5 cm.

*Depth.*—2.5 cm.

*Total diameter of 'disc'.*—No disc showing.

*Receptacle height.*—0.7 cm.

*Receptacle diameter.*—0.5 cm at widest point.

Ray florets:

*Average quantity of florets.*—Approximately 175 in numerous whorls.

*Color of florets, upper surface.*—RHS 8C becoming RHS 8B with RHS 7C in the center.

*Lower surface.*—RHS 8C with hint of RHS 34C.

*Length.*—2.4-2.6 cm.

*Width.*—0.5 cm at widest point.

*Shape.*—Spoon.

*Apex shape.*—Emarginate to some praemorse.

*Margin.*—Entire.

*Texture, upper surface.*—Papillose.

*Lower surface.*—Papillose.

Disc florets:

*Average quantity of florets.*—0.

*Color of florets.*—N/A.

*Length.*—N/A.

*Width.*—N/A.

*Shape.*—N/A.

*Apex shape.*—N/A.

Phyllaries:

*Quantity.*—Approximately 50.

*Color, upper surface.*—RHS 144A.

*Lower surface.*—RHS 137A but lighter.

*Length.*—0.1-0.5 cm.

*Width.*—0.4-0.5 cm.

*Shape.*—Lanceolate to linear.

*Apex shape.*—Acute.

*Based.*—Fused.

*Margins.*—Entire.

*Texture, upper surface.*—Glabrous.

*Lower surface.*—Bifid.

Reproductive organs:

*Pistil.*—1.

*Length.*—0.4 cm.

*Style color*.—RHS 1B.
*Style length*.—0.4 cm.
*Stigma color*.—RHS 1B with a little more green.
*Stigma shape*.—Bi-parted.
*Ovary color*.—Not observed.
*Stamens*.—1.
*Color of filaments*.—RHS 1C.
*Length filaments*.—0.2 cm.
*Anther color*.—RHS 3C.
*Anther length*.—0.1 cm.
*Anther shape*.—Oblong.
*Color of pollen*.—Not observed.
*Pollen amount*.—Not observed.
*Fertility/seed set*.—Has not been observed on this hybrid.

Disease/pest resistance: Disease/pest resistance has not been observed on this hybrid.

What is claimed is:

1. A new and distinct variety of *Chrysanthemum* plant named 'Syelect Ambe' substantially as illustrated and described herein.

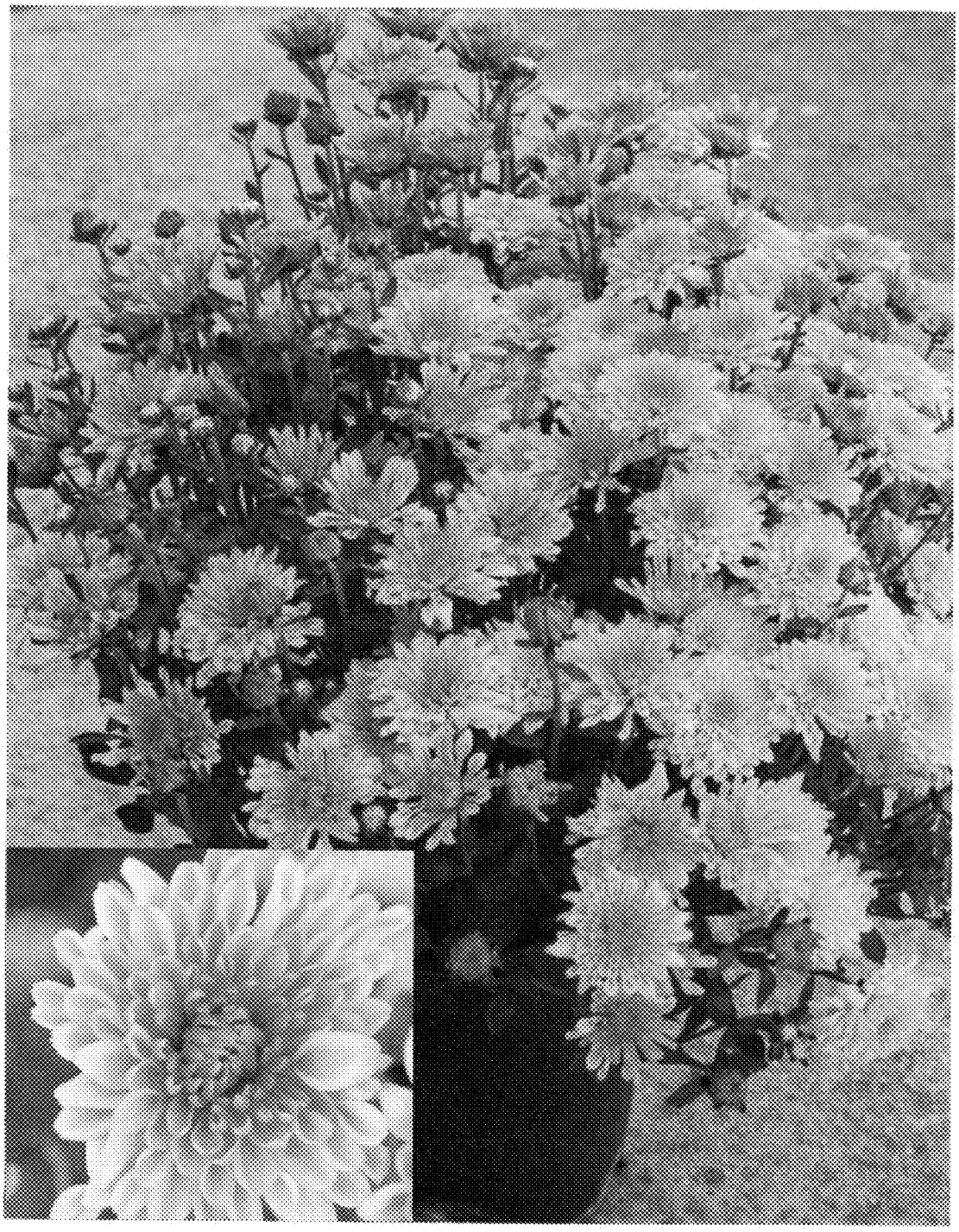

* * * * *